United States Patent [19]
Webster et al.

[11] Patent Number: 5,101,162
[45] Date of Patent: Mar. 31, 1992

[54] METHOD AND APPARATUS FOR TESTING THE RESPONSE OF A STRESS WAVE SENSOR

[75] Inventors: John R. Webster, Derby; Michael Sadler, Burton on Trent, both of England

[73] Assignee: Rolls-Royce PLC, London, England

[21] Appl. No.: 637,703

[22] Filed: Jan. 7, 1991

[30] Foreign Application Priority Data

Feb. 16, 1990 [GB] United Kingdom ............... 9003569

[51] Int. Cl.⁵ .................. G01N 29/04; G01D 18/00
[52] U.S. Cl. ................................ 324/618; 324/537; 324/601; 324/609; 340/683; 340/515; 73/1 DV
[58] Field of Search .............. 73/1 DV; 340/515, 683, 340/682; 324/601, 609, 618, 537

[56] References Cited

U.S. PATENT DOCUMENTS

| | | | |
|---|---|---|---|
| 3,531,977 | 10/1970 | Chaskelis | 73/1 DV |
| 3,924,456 | 12/1975 | Vahaviolos . | |
| 4,043,176 | 12/1975 | Graham . | |
| 4,240,281 | 12/1980 | Lather | 73/1 DV |
| 4,391,124 | 7/1983 | Drost | 73/1 DV |
| 4,445,361 | 5/1984 | Moffett | 73/1 DV |
| 4,567,747 | 2/1986 | Matay | 73/1 DV |
| 4,677,595 | 6/1987 | Obayashi | 73/1 DV |
| 4,694,680 | 9/1987 | Takeuchi | 73/1 DV |

FOREIGN PATENT DOCUMENTS

| | | |
|---|---|---|
| 0393828 | 10/1990 | European Pat. Off. . |
| 0222260 | 9/1988 | Japan ........ 73/1 DV |
| 2008755 | 11/1978 | United Kingdom . |
| 2137751 | 3/1984 | United Kingdom . |
| 2183037 | 11/1985 | United Kingdom . |
| 2199949 | 7/1988 | United Kingdom . |

Primary Examiner—Kenneth A. Wieder
Assistant Examiner—Jose M. Solis
Attorney, Agent, or Firm—Cushman, Darby & Cushman

[57] ABSTRACT

The invention relates to a method and apparatus for testing the response of a stress wave sensor to check that the transducer and amplifier are working satisfactorily.

A pulse generator is connected to the stress wave sensor at a point between the transducer and the amplifier. The pulse generator supplies an electrical pulse to the stress wave sensor. A pulse cancelling device prevents the electrical pulse going directly to the amplifier. The electrical pulse causes the transducer to emit stress wave energy into a structure to which the transducer is acoustically coupled. The transducer detects the stress wave propagating in the structure and supplies an electrical signal to the amplifier. The electrical signal is amplified by the amplifier and demodulated by demodulator. A processor measures the peak and area of the demodulated amplified electrical signal and comares them with stored values. The processor may produce a warning signal, or supply a feedback signal to the amplifier if the stress wave sensor is not operating satisfactorily.

24 Claims, 3 Drawing Sheets

METHOD AND APPARATUS FOR TESTING THE RESPONSE OF A STRESS WAVE SENSOR

The present invention relates to a method and an apparatus for testing the response of a stress wave sensor or acoustic emission system.

Stress wave sensors are used for monitoring of machinery, processes or structures, and it is desirable for stress wave sensors to be installed for long term monitoring of machinery, processes or structures. In such long term monitoring of machinery, processes or structures, it is highly desirable to have a procedure to confirm that the stress wave sensor is working satisfactorily. It is necessary to confirm that the stress wave transducer and amplifier which make up part of the stress wave sensor are functioning satisfactorily.

Common methods used to confirm the operation of stress wave sensors, or acoustic emission sensors are the use of a breaking pencil lead, a gas jet, ball impacts, laser pulses and electrical discharges which artificially introduce stress waves into a structure to which the sensor is acoustically coupled. A further method uses periodically applied stress wave pulses from another electrically excited stress wave or acoustic emission transducer. However such methods require an operator to check the stress wave sensor, or acoustic emission sensor, is working satisfactorily.

The present invention seeks to provide a novel method and apparatus for testing the response of a stress wave sensor.

Accordingly the present invention provides a method of testing the response of a stress wave sensor, the stress wave sensor comprising a transducer acoustically coupled to a structure and an amplifier, the transducer and amplifier being electrically connected in series, the method comprising supplying at least one electrical pulse to emit a stress wave signal into the structure, preventing the supplied electrical pulse being received directly by the amplifier, an operative transducer detecting the stress wave signal after propagating through the structure and producing an electrical signal, supplying the electrical signal to the amplifier for amplification of the electrical signal, demodulating the amplified electrical signal, analysing the demodulated amplified electrical signal to measure the peak amplitude of the demodulated amplified electrical signal and to measure the area of the demodulated amplified electrical signal which indicate the transducer and amplifier condition or to measure the decay slope of the demodulated amplified electrical signal which corresponds to the damping applied to the structure and transducer.

A feedback signal may be supplied to the amplifier to adjust the gain of the amplifier.

A warning signal may be generated if the stress wave sensor is not operating satisfactorily.

The present invention also provides an apparatus for testing the response of a stress wave sensor comprising a transducer acoustically coupled to a structure, an amplifier and a demodulator arranged electrically in series, the apparatus comprising means to supply at least one electrical pulse and means to emit a stress wave signal into the structure, the apparatus being arranged to prevent the supplied electrical pulse being received directly by the amplifier, an operative transducer being arranged to detect the stress wave signal after propagating through the structure and being arranged to produce an electrical signal, the transducer being arranged to supply the electrical signal to the amplifier for amplification, the amplified electrical signal being supplied to the demodulator for demodulation, the demodulated amplified electrical signal being supplied to a processor, the processor being arranged to measure the peak amplitude of the demodulated amplified electrical signal and to measure the area of the demodulated amplified electrical signal which indicate the transducer and amplifier condition or to measure the decay slope of the demodulated amplified electrical signal which corresponds to the damping applied to the structure and transducer. A pulse generator may be arranged to be electrically connected to the stress wave sensor at a point electrically between the transducer and the amplifier, the pulse generator being arranged to supply at least one electrical pulse to the stress wave sensor, an operative transducer being caused to emit a stress wave signal into the structure by the electrical pulse, the transducer being arranged to detect the stress wave signal after propagating through the structure and being arranged to produce an electrical signal, a pulse cancelling device being positioned electrically between said point and the amplifier to prevent the at least one electrical pulse being received by the amplifier.

The means to emit a stress wave signal into the structure may comprise a second transducer acoustically coupled to the structure, a pulse generator arranged to be electrically connected to the second transducer, the pulse generator being arranged to supply the at least one electrical pulse to the second transducer, the second transducer being caused to emit stress wave signal into the structure by the electrical pulse.

The processor may compare the measured values of the peak amplitude and area of the demodulated amplified electrical signal with stored ranges of acceptable values.

The processor may compare the measured value of the decay slope of the demodulated amplified electrical signal with a stored range of acceptable values.

The processor may supply a feedback signal to the amplifier to adjust the gain of the amplifier.

The processor may generate a warning signal if the stress wave sensor is not operating satisfactorily.

BRIEF DESCRIPTION OF THE DRAWING

The present invention will be more fully described by way of example with reference to the accompanying drawings, in which.

DESCRIPTION OF THE PREFERRED EMBODIMENT

Figure 1:
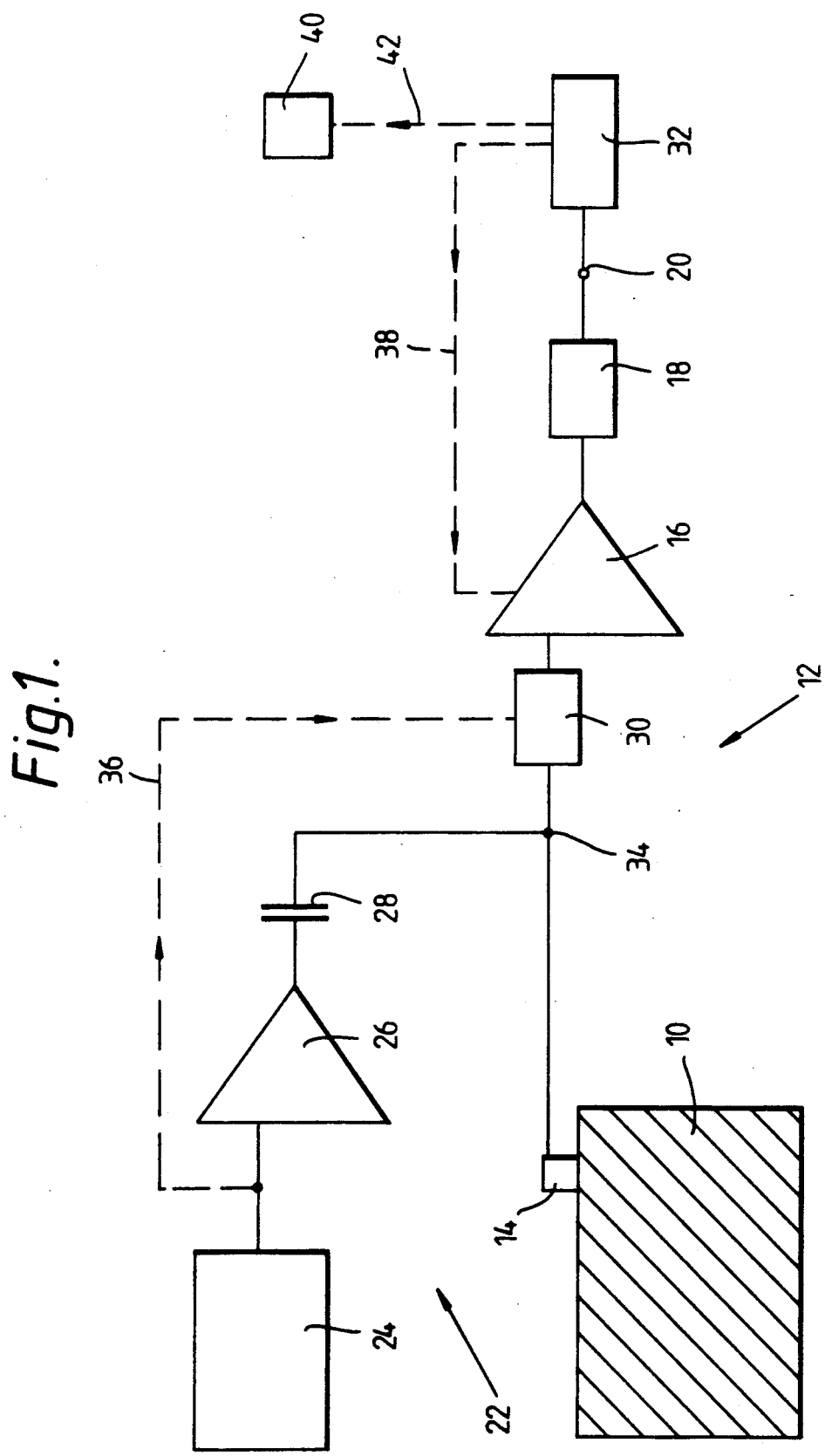
FIG. 1 is an electrical circuit representative of a stress wave sensor according to the present invention.

An apparatus 22 for testing the response of a stress wave sensor 12 is shown in FIG. 1. The stress wave sensor 12 comprises a piezoelectric type stress wave transducer 14, an amplifier 16 and a demodulator 18, electrically connected in series. The demodulator 18 has an output terminal 20. The transducer 14 is acoustically coupled to a structure 10. The transducer 14 detects stress waves propagating in the structure 10 and produces an electrical signal corresponding to the stress wave propagating in the structure 10. The electrical signal is amplified by the amplifier 16 and supplied to the demodulator 18. The demodulator 18 envelopes the amplified electrical signal and supplies it to the output terminal 20. The demodulated amplified electrical signal may then be processed to analyse the stress waves propagating in the structure 10 to gather information concerning the structure.

The apparatus 22 for testing the response of the stress wave sensor 12 comprises a pulse generator 24, which for example may be a high speed CMOS monostable, an amplifier 26, a decoupler 28, a pulse cancelling device 30 and a processor 32. The pulse generator 24, the amplifier 26 and the decoupler 28 are arranged electrically in series, and the output of the decoupler 28 is electrically connected to the stress wave sensor 12 at a point 34 electrically between the transducer 14 and the amplifier 16. The pulse cancelling device 30 is positioned electrically between the point 34 and the amplifier 16, and the processor 32 is electrically connected to the output terminal 20.

The pulse generator 24 generate short electrical pulses which are amplified by the amplifier 26 and supplied via the decoupler 28 to the stress wave sensor 12 at the point 34. The amplified short electrical pulses are supplied only to the transducer 14, because electrical signals from the pulse generator 24 are supplied to the pulse cancelling device 30 via an electrical connection 36. The pulse cancelling device 30 switches off the input to the amplifier 16 for short periods of time in order to protect the amplifier 16 from the effects of the electrical pulses and to remove the electrical energy of the pulses from the demodulated amplified electrical signal. The amplified short electrical pulses supplied to the transducer 14 cause the transducer 14 to emit bursts of stress wave energy into the structure 10. The transducer 14 then detects the stress waves after propagation through the structure 10, and produces an electrical signal. The electrical signal is supplied to the amplifier 16, for amplification, and the amplified electrical signal is enveloped by the demodulator 18. The demodulated amplified electrical signal is then supplied to the processor 32 for processing.

Figure 2:
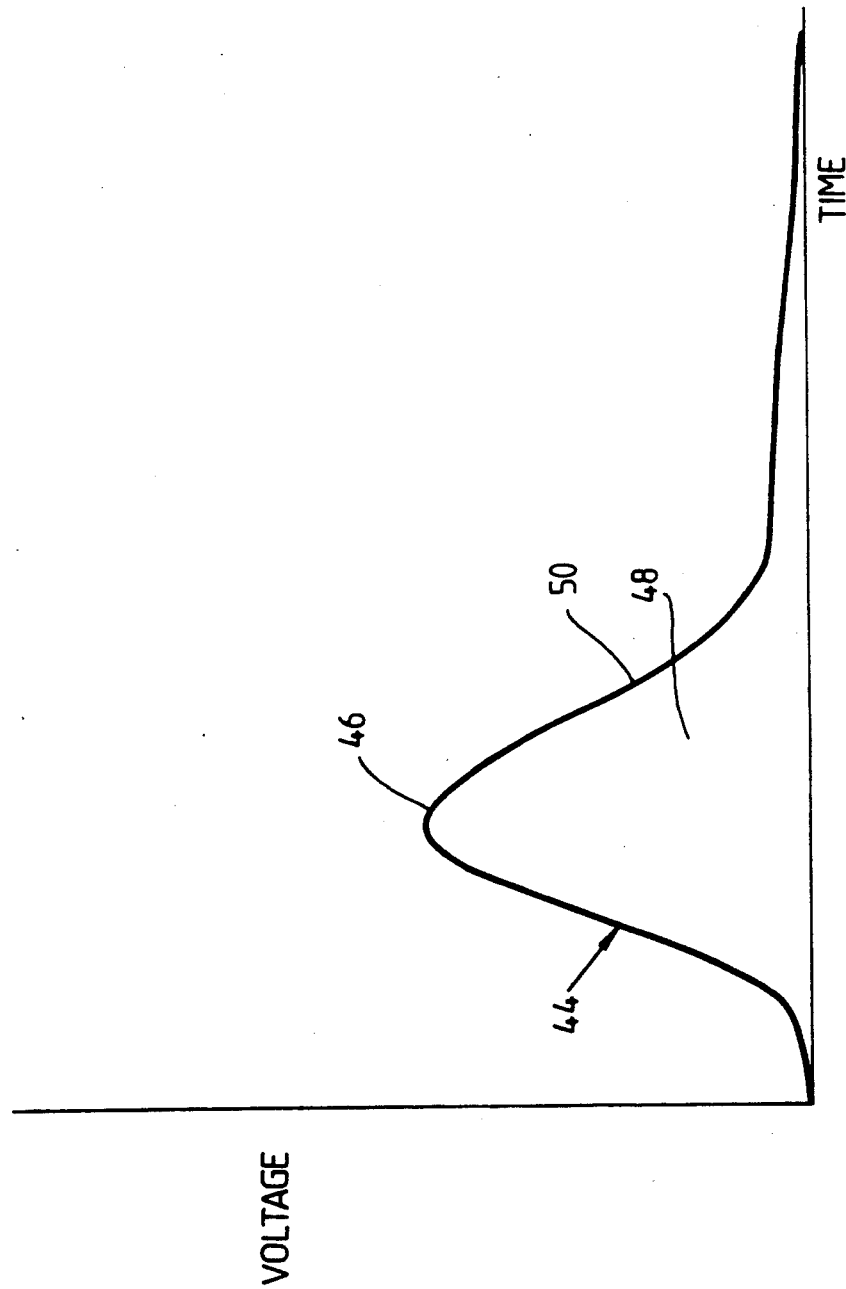
FIG. 2 is a graph of voltage against time showing the output envelope from an operative stress wave sensor as a result of an electrical pulse.

A demodulated amplified electrical signal 44 prior to supplying to the processor 32 is shown in FIG. 2. The demodulated amplified electrical signal has a peak amplitude 46, an area 48 under the curve of the electrical signal and a decay slope 50. The peak amplitude 46, the area 48 under the curve and the decay slope 50 of the demodulated amplified electrical signal 44 are all sensitive to changes which may affect the operation of the stress wave sensor 12. The peak amplitude 46 and the area 48 under the curve are dependent upon the condition of the transducer, the amplifier and the demodulator of the stress wave sensor. The decay slope 50 is predominantly dependent upon damping of the structure 10 to which the stress wave sensor is coupled. The decay slope 50 may change in response to contaminants, such as oil, other materials or structures, coming into contact with the structure 10.

The processor 32 is therefore arranged to measure the peak amplitude, the area under the curve and the decay slope of the demodulated amplified electrical signal. The processor 32 then compares the measured values of the peak amplitude, the area under the curve and the decay slope of the demodulated amplified electrical signal with stored ranges of acceptable values for the peak amplitude, area and decay slope. If all the measured values of peak amplitude, area and decay slope are in their respective range of acceptable values then the stress wave sensor is operating satisfactorily. If any one or more of the values of peak amplitude, area and decay slope is not in the range of acceptable values then the stress wave sensor is not operating satisfactorily. If the stress wave sensor is not operating satisfactorily, this may be caused by a reduction in sensitivity of the transducer, a loss of gain of the amplifier or changes to the damping applied to the structure.

The processor 32 may be arranged to produce a warning signal to indicate that the stress wave sensor 12 is not operating satisfactorily. The warning signal is supplied to an indicator 40 i.e. a light or alarm via an electrical connection 42. Equally well the processor 32 may be arranged to produce a feedback signal to adjust the sensitivity of the stress wave sensor. The feedback signal is supplied to the amplifier 16 via an electrical connection 38 to adjust the gain of the amplifier 16. Thus the apparatus 22 for testing the stress wave sensor automatically checks the operation of the stress wave sensor, without the use of an operator and confirms that the stress wave sensor is operating satisfactorily or indicates that there is a fault, or adjusts the sensitivity of the stress wave sensor to compensate for changes in transducer sensitivity, amplifier gain or damping of the structure. This allows the stress wave sensor to operate unattended for extended periods.

Figure 3:
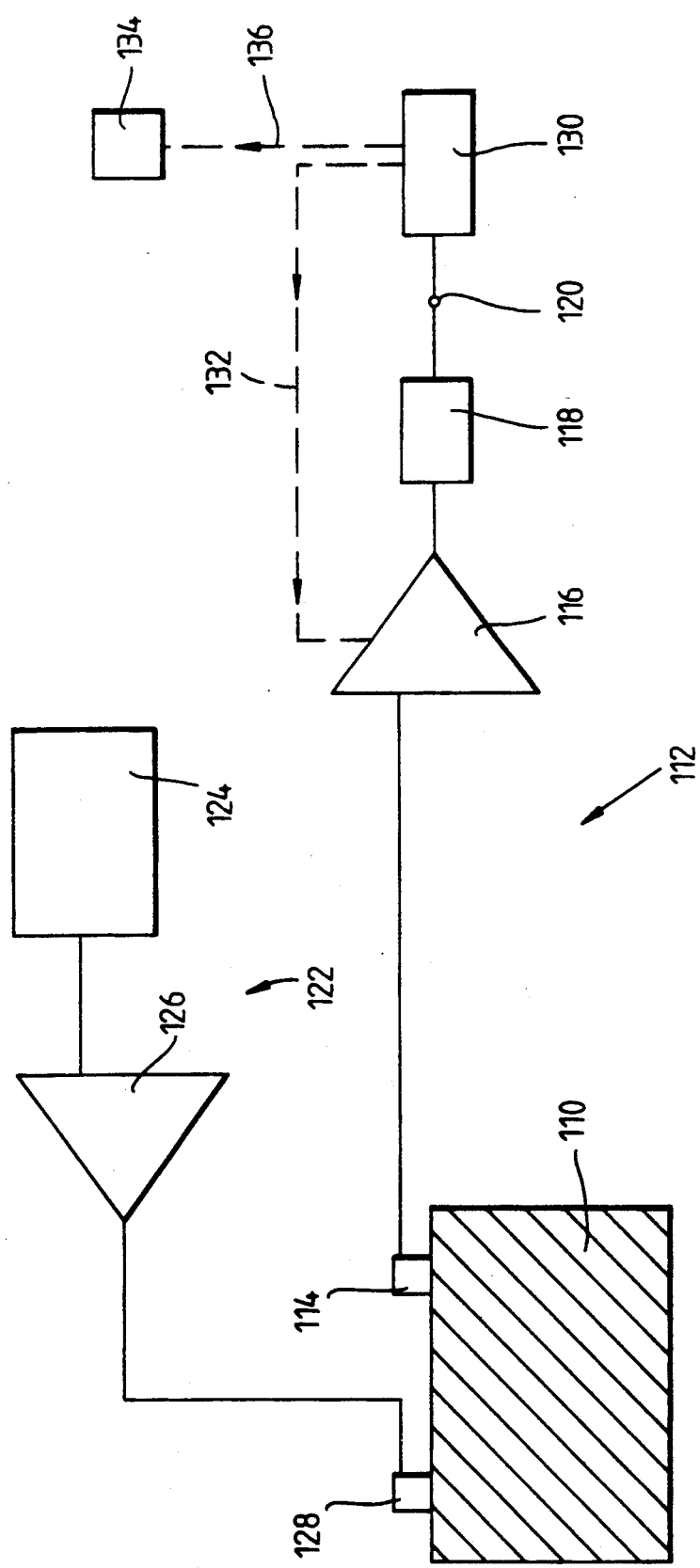
FIG. 3 is an electrical circuit representative of an alternative stress wave sensor according to the present invention.

A further apparatus 122 for testing the response of a stress wave sensor 112 is shown in FIG. 3. The stress wave sensor 112 comprises a piezoelectric type stress wave transducer 114, an amplifier 116 and a demodulator 118 electrically connected in series. The demodulator 118 has an output terminal 120. The transducer 114 is acoustically coupled to a structure 110. The transducer 114 detects stress waves propagating in the structure 110 and produces an electrical signal corresponding to the stress wave propagating in the structure 110. The electrical signal is amplified by the amplifier 116 and then enveloped by the demodulator 118. The demodulated amplified electrical signal is supplied to the output terminal 120 and is processed to gather information concerning the structure.

The apparatus 122 for testing the response of the stress wave sensor 112 comprises a pulse generator 124, an amplifier 126, a transducer 128 and a processor 130. The pulse generator 124, the amplifier 126 and the transducer 128 are arranged electrically in series. The processor 130 is electrically connected to the output terminal 120. The transducer 128 is acoustically coupled to the structure 110.

The pulse generator 124 generates short electrical pulses which are amplified by the amplifier 26 and supplied to the transducer 128. The transducer 128 is caused to emit bursts of stress wave energy into the structure 110 by the short electrical pulses. The transducer 114 then detects the stress waves after propagation through the structure 110, and produces an electrical signal. The electrical signal is supplied to the amplifier 116 for amplification, and the amplified electrical signal is enveloped by the demodulator 118. The demodulated amplified electrical signal is then supplied to the processor 130 for processing.

The processor 130 is arranged to measure the peak amplitude, the area under the curve and the decay slope of the demodulated amplified electrical signal. The processor then compares the measured values of the peak amplitude, the area under the curve and the decay slope of the demodulated amplified electrical signal with stored ranges of acceptable values for the peak amplitude, area and decay slope.

The processor 130 may supply a feedback signal to the amplifier 116 via connection 132 or supply a warning signal to an indicator 134 via connection 136 when the sensor is not operating satisfactorily. The advantage of using the FIG. 3 arrangement is that the need for the pulse cancelling device is removed.

Although the description has referred only to a single electrical pulse the testing of the response of the stress wave sensor may be carried out using more than one pulse. If continuous pulsing of the stress wave sensor is used, the square root of the detected RMS demodulated amplified electrical signal may be measured to indicate the efficiency of the acoustic coupling between the transducer and the structure.

Although the description has referred to the transducer being acoustically coupled to a structure, it may equally well be acoustically coupled to a machine or a process, and therefore the term structure is intended to include a structure, a machine or a process. The term stress wave sensor is intended to include stress wave sensors and acoustic emission sensors.

We claim:

1. A method of testing the response of a stress wave sensor, the stress wave sensor comprising a transducer and an amplifier, the transducer being acoustically coupled to a structure, the transducer and amplifier being electrically connected in series, the method comprising the steps of: supplying at least one electrical pulse to emit a stress wave signal into the structure, preventing the supplied electrical pulse from being received directly by the amplifier, an operative transducer detecting the stress wave signal after propagating through the structure and producing an electrical signal, supplying the electrical signal to the amplifier for amplification of the electrical signal, demodulating the amplified electrical signal, analyzing the demodulated amplified electrical signal to measure the peak amplitude of the demodulated amplified electrical signal and to measure the area of the demodulated amplified electrical signal to indicate the transducer and amplifier condition.

2. A method as claimed in claim 1 in which the decay slope of the demodulated amplified electrical signal is measured which corresponds to the damping applied to the structure and transducer.

3. A method as claimed in claim 1 in which a feedback signal is supplied to the amplifier to adjust the gain of the amplifier.

4. A method as claimed in claim 1 in which a warning signal is generated if the stress wave sensor is not operating satisfactorily.

5. A method as claimed in claim 1 in which a plurality of electrical pulses are supplied to the stress wave sensor, the analyzing of the demodulated amplified electrical signal comprises measuring the RMS value of the demodulated amplified electrical signal which corresponds to the efficiency of acoustic coupling between the transducer and the structure.

6. A method of testing the response of a stress wave sensor, the stress wave sensor comprising a transducer and an amplifier, the transducer being acoustically coupled to a structure, the transducer and amplifier being electrically connected in series, the method comprising the steps of: supplying at least one electrical pulse to emit a stress wave signal into the structure, preventing the supplied electrical pulse being received directly by the amplifier, an operative transducer detecting the stress wave signal after propagating through the structure and producing an electrical signal, supplying the electrical signal to the amplifier for amplification of the electrical signal, demodulating the amplified electrical signal, analyzing the demodulated amplified electrical signal to measure the decay slope of the demodulated amplified electrical signal which corresponds to the damping applied to the structure and transducer.

7. A method as claimed in claim 6 in which a feedback signal is supplied to the amplifier to adjust the gain of the amplifier.

8. A method as claimed in claim 6 in which a warning signal is generated if the stress wave sensor is not operating satisfactorily.

9. A method as claimed in claim 6 in which a plurality of electrical pulses are supplied to the stress wave sensor, the analyzing of the demodulated amplified electrical signal comprises measuring the RMS value of the demodulated amplified electrical signal which corresponds to the efficiency of acoustic coupling between the transducer and the structure.

10. An apparatus for testing the response of a stress wave sensor, the stress wave sensor comprising a transducer, an amplifier and a demodulator arranged electrically in series, the transducer is acoustically coupled to a structure, the apparatus comprising means to supply at least one electrical pulse, means to emit a stress wave signal into the structure, the apparatus being arranged to prevent the supplied electrical pulse being received directly by the amplifier, the means to supply at least one electrical pulse is arranged to supply at least one electrical pulse to the means to emit a stress wave signal into the structure such that a stress wave is generated in the structure, an operative transducer is arranged to detect the stress wave signal after propagating through the structure and is arranged to produce an electrical signal, the transducer is arranged to supply the electrical signal to the amplifier for amplification, the amplified electrical signal is supplied to the demodulator for demodulation, the demodulated amplified electrical signal is supplied to a processor, the processor is arranged to measure the peak amplitude of the demodulated amplified electrical signal and to measure the area of the demodulated amplified electrical signal which indicate the transducer and amplifier condition.

11. An apparatus as claimed in claim 10 in which the processor is arranged to measure the decay slope of the demodulated amplified electrical signal which corresponds to the damping applied to the structure and transducer.

12. An apparatus as claimed in claim 10 in which the means to emit a stress wave signal into the structure comprises a second transducer acoustically coupled to the structure, a pulse generator is arranged to be electrically connected to the second transducer, the pulse generator is arranged to supply the at least one electrical pulse to the second transducer, the second transducer being caused to emit a stress wave signal into the structure by the electrical pulse.

13. An apparatus as claimed in claim 10 in which a pulse generator is arranged to be electrically connected to the stress wave sensor at a point electrically between the transducer and the amplifier, the pulse generator is arranged to supply the at least one electrical pulse to the stress wave sensor, an operative transducer being caused to emit a stress wave signal into the structure by the electrical pulse, the transducer is arranged to detect the stress wave signal after propagating through the structure and is arranged to produce an electrical signal, a pulse cancelling device is positioned electrically between said point and the amplifier to prevent the at least one electrical pulse being received directly by the amplifier.

14. An apparatus as claimed in claim 10 in which the processor compares the measured values of the peak amplitude and area of the demodulated amplified electrical signal with stored ranges of acceptable values.

15. An apparatus as claimed in claim 11 in which the processor compares the measured value of the decay slope of the demodulated amplified electrical signal with a stored range of acceptable values.

16. An apparatus as claimed in claim 10 in which the processor supplies a feedback signal to the amplifier to adjust the gain of the amplifier.

17. An apparatus as claimed in claim 10 in which the processor generates a warning signal if the stress wave sensor is not operating satisfactorily.

18. An apparatus as claimed in claim 10 in which a plurality of electrical pulses are supplied to the stress wave sensor, the processor measures the RMS value of the demodulated amplified electrical signal which corresponds to the efficiency of acoustic coupling between the transducer and the structure.

19. An apparatus for testing the response of a stress wave sensor, the stress wave sensor comprising a transducer, an amplifier and a demodulator arranged electrically in series, the transducer is acoustically coupled to a structure, the apparatus comprising means to supply at least one electrical pulse, means to emit a stress wave signal into the structure, the apparatus being arranged to prevent the supplied electrical pulse being received directly by the amplifier, the means to supply at least one electrical pulse is arranged to supply at least one electrical pulse to the means to emit a stress wave signal into the structure such that a stress wave is generated in the structure, an operative transducer is arranged to detect the stress wave signal after propagating through the structure and is arranged to produce an electrical signal, the transducer is arranged to supply the electrical signal to the amplifier for amplification, the amplified electrical signal is supplied to the demodulator for demodulation, the demodulated amplified electrical signal is supplied to a processor, the processor is arranged to measure the decay slope of the demodulated amplified electrical signal which corresponds to the damping applied to the structure and transducer.

20. An apparatus as claimed in claim 19 in which the means to emit a stress wave signal into the structure comprises a second transducer acoustically coupled to the structure, a pulse generator is arranged to be electrically connected to the second transducer, the pulse generator is arranged to supply the at least one electrical pulse to the second transducer, the second transducer being caused to emit a stress wave signal into the structure by the electrical pulse.

21. An apparatus as claimed in claim 19 in which a pulse generator is arranged to be electrically connected to the stress wave sensor at a point electrically between the transducer and the amplifier, the pulse generator is arranged to supply the at least one electrical pulse to the stress wave sensor, an operative transducer being caused to emit a stress wave signal into the structure by the electrical pulse, the transducer is arranged to detect the stress wave signal after propagating through the structure and is arranged to produce an electrical signal, a pulse cancelling device is positioned electrically between said point and the amplifier to prevent the at least one electrical pulse being received directly by the amplifier.

22. An apparatus as claimed in claim 19 in which the processor compares the measured value of the decay slope of the demodulated amplified electrical signal with a stored range of acceptable values.

23. An apparatus as claimed in claim 19 in which the processor generates a warning signal if the stress wave sensor is not operating satisfactorily.

24. An apparatus as claimed in claim 19 in which a plurality of electrical pulses are supplied to the stress wave sensor, the processor measures the RMS value of the demodulated amplified electrical signal which corresponds to the efficiency of acoustic coupling between the transducer and the structure.

* * * * *